United States Patent [19]
de Juan, Jr.

[11] Patent Number: 5,980,929
[45] Date of Patent: Nov. 9, 1999

[54] USE OF A PROTEIN TYROSINE KINASE PATHWAY INHIBITOR IN THE TREATMENT OF RETINAL ISCHMEMIA OR OCULAR INFLAMMATION

[75] Inventor: Eugene de Juan, Jr., Phoenix, Md.

[73] Assignee: Johns Hopkins University, School of Medicine, Baltimore, Md.

[21] Appl. No.: 09/042,440

[22] Filed: Mar. 13, 1998

[51] Int. Cl.$^6$ .................................. A61F 2/14; A61F 2/02
[52] U.S. Cl. ............................................ 424/427; 424/423
[58] Field of Search ...................................... 424/423, 427

[56] References Cited

U.S. PATENT DOCUMENTS 5,637,703  6/1997  Mazurek et al. .

FOREIGN PATENT DOCUMENTS

WO 97/30701  8/1997  WIPO .

OTHER PUBLICATIONS

Barnes, "Effect of Genistein on In Vitro and In Vivo Models of Cancer," *J. Nutr.* 125:777S–783S (1995).
Barnes et al., "Biochemical Targets of the Isoflavone Genistein in Tumor Cell Lines," *PSEMB* 208: 103–108 (1995).
Burke, Jr. "Protein–Tyrosine Kinase Inhibitors," *Drugs of the Future* 17(2): 119–131 (1992).
Coward et al., "Genistein, Daidzein, and Their αBlycoside Conjugates: Antitumor Isoflavones in Soybean Foods from American and Asian Diets," *J. Argic. Food Chem.* 41: 1961–1967 (1993).
Cunnigham et al. "Synthesis and Biological Evaluation of a Series of Flavones Designed as Inhibitors of Protein Tyrosine Kinases," *Anti–Cancer Drug Design* 7:365–384 (1992)
Filipeanu et al., "Multiple Effects of Tyrosine Kinase Inhibitors on Vascular Smooth Muscle Contraction," *European Journal of Pharmacology* 281(1):29–35 (1995) Abstract.
Fotsis et al., "Genistein, A Dietary Ingested Isoflavonoid Inhibits Cell–Proliferation and In–Vitro Angiogenesis," Journal of Nutrition 125(3): 790–797 (1995) (Abstract).
Fotsis et al., "Genistein, A Dietary–Derived Inhibitor of *In Vitro* Angiogenesis," *PNAS USA* 90: 2690–2694 (1993).
Hayashi et al., "Activation of Protein Tyrosine Phosphorylation After Retinal Branch Vein Occlusion in Cats," *Investigative Ophthalmology & Visual Science* 38(2): 372–380 (1997).
Hayashi et al., "Increase of Protein Tyrosine Phosphorylation in Rat Retina After Ischemia–Reperfusion Injury," *Investigative Ophthalmology & Visual Science* 7(11): 2146–2156 (1996).
Hayashi et al., "Genistein, a Protein Tyrosine Kinase Inhibitor, Amerliorates Retinal Degeneration After Ischemia–Reperfusion Injury in Rat," *Investigative Ophthalmology & Visul Science* 38(6): 1193–1202 (1997).
Hayashi et al., "Role of Protein Tyrosine Phosphorylation in Rat Corneal Neovascularization," *Grafe's Arch. Clin. Exp. Ophthalmol.* 235: 460–467 (1997).
Hayashi et al., "Genistein, A Protein Tyrosine Kinase Inhibitor, Ameliorates Retinal Degeneration After Ischemia–Reperfusion Injury in rat," *Investigative Ophthalmology and Visual Science* 38 (4):489–B400 (1997) Abstract.
Herman et al., "Soybean Phytoestrogen Intake and Cancer Risk," *J. Nutr.* 125:757S–770S (1995).
Kennedy, "The Evidence of Soybena Products as Cancer Preventive Agents," *J. Nutr.* 125: 733S–742S (1995).
Kindy, "Inhibition of Tyrosine Phosphorylation Prevents Delayed Neuronal Agents Death Following Cerebal Ischemia," *Journal of Cerebal Blood Flow and Metabolism* 13:372–377 (1993).
Koroma et al., "Changes Associated With Tyrosine Phosphorylating During Short–Term Hypoxia in Retinal Microvascular Endothelial Cells In Vitro," *Journal of Cellular Biochemistry* 59: 123–132 (1995).
Koroma et al., "Phosphotyrosine Inhibition and Control of Vascular Endothelial Cell Proliferation by Genistein," *Biochemical Pharmacology* 48(4):809–818 (1994).
Lamartiniere et al., "Neonatal Genistein Chemoprevents Mammary Cancer," *PSEBM* 208: 120–123 (1995).
Levitzki et al., "Tyrosine Kinase Inhibition: An Approach to Drug Development," *Science* 267:1782–1790 (1995).
Lu et al., "Effects of Soya Consumption for One Month on Steroid Hormones in Premenopausal Women: Implications for Breast Cancer Risk Reduction," *Cancer Epidemiology, Biomakers & Prevention* 5: 63–70 (1996).
Moritoki et al., "Possible Involvement of Tyrosine Kinase in the LPS–Promoted Initiation of L–arginine–Induced Relaxation of Rat Aorta Mediated by Induction of $N_o$ Synthase," *Life Sciences* 57(11): PL125–130 (1995) (Abstract).
Ohira et al., "Retinal Ischemia and Cell Proliferation in the Rat: The Role of Soluble Mitogens," *Graefe's Arch Clin. Exp. Ophthalmol.* 228: 195–199 (1990).
Raines et al., "Biology of Atherosclerotic Plaque Formation: Possible Role of Growth Factors in Lesion Development and the Potential Impact of Soy," *Journal of Nutrition* 125(3 Suppl.): 624S–630S (1995) (Abstract).
Steele et al., "Cancer Chemoprevention Agent Development Strategies for Genistein," *J. Nutr.* 125:713S–716S (1995).
Steusloff et al., "Modulation of Ca2+ Sensitivity in Smooth Muscle by Genistein and Protein Tyrosine Phosphorylation," *Archives of Biochemistry & Biophysics* 320(2): 236–242 (1995) (Abstract).

(List continued on next page.)

*Primary Examiner*—Carlos A. Azupuru

*Attorney, Agent, or Firm*—Leydig, Voit & Mayer, Ltd.

[57] ABSTRACT

The present invention is directed to methods for the prophylactic and therapeutic treatment of retinal ischemia and retinal inflammation. The methods involve the administration of an inhibitor of the protein tyrosine kinase pathway to an animal, such as a mammal, in particular a human, in an amount sufficient to treat the retina for ischemia or inflammation prophylactically or therapeutically. The inhibitor of the protein tyrosine kinase pathway is preferably genistein or an analogue or prodrug thereof or a pharmaceutically acceptable salt of any of the foregoing.

56 Claims, No Drawings

OTHER PUBLICATIONS

Wilcox et al., "Thrombic Mechanisms in Atherosclerosis: Potential Impact of Soy Proteins," *Journal of Nutrition* 125(3): 631S–638S (1995) (Abstract).

Xiong et al., "Modulation of Ca(2+)–activated K+ Channel Activity by Tyrosine Kinase Inhibitors in Vascular Smooth Muscle Cell," *European Journal of Pharmacology* 290(2): 117–123 (1995) (Abstract).

USE OF A PROTEIN TYROSINE KINASE PATHWAY INHIBITOR IN THE TREATMENT OF RETINAL ISCHMEMIA OR OCULAR INFLAMMATION

TECHNICAL FIELD OF THE INVENTION

The present invention relates to methods for the prophylactic and therapeutic treatment of retinal ischemia and ocular inflammation.

BACKGROUND OF THE INVENTION

Retinal ischemia occurs as a result of occlusion of a retinal blood vessel, such as occlusion of the central retinal vein or artery or a branch retinal vein or artery. Occlusion of blood vessels results in low oxygen tension in adjacent tissues, which triggers a signaling cascade that culminates in neovascularization, capillary nonperfusion and macular edema (Koroma et al., *J. Cell. Biochem.* 59: 123–132 (1995)). Retinal vein occlusion can occur in patients suffering from hypertension and hyperlipidemia and not infrequently can occur in diabetic patients, in particular patients suffering from type II diabetes. In type I diabetic patients, retinal vein occlusion and chronic hypoxia may be related to other microvascular complications of diabetes, such as diabetic retinopathy and proteinuria, although hypertension and a trend to increased hyperlipidemia are strikingly highly prevalent in diabetic patients with retinal vein occlusion (Dodson et al., *European J. Ophthalmol.* 3(3): 109–113 (1993)).

Tyrosine-phosphorylated proteins, vascular endothelial growth factor, and basic fibroblast growth factor increase after occlusion of a retinal blood vessel, especially within the occluded blood vessel. In addition, two signal proteins in tyrosine kinase pathways, namely phospholipase $C_\gamma$ and mitogen-activated protein kinase, are activated (Hayashi et al., *Invest. Ophthalmol. Vis. Sci.* 37(11): 2146–2156 (1996)).

Tyrosine phosphorylation of cellular proteins and changes in the expression of the fibroblast growth factor receptor have been suggested to play a role in the activation of endothelial cell proliferation by short-term hypoxia, such as that resulting from retinal blood vessel occlusion (Koroma et al. (1995), supra). Endothelial response can run the gamut from increased cell proliferation and synthesis of IL-1α (Shreeniwas et al., *J. Clin Invest.* 90: 2333–2339 (1992)) and upregulation of TGFβ (Santilli et al., *Ann. Vasc. Surg.* 5: 429–438 (1991)) to increases in glucose transporter (Loike et al., *Am. J. Physiol.* 263: C326–C333 (1992)), intracellular calcium (Arnould et al., *J. Cell. Physiol.* 152: 215–221 (1992)), prostaglandins (Michiels et al., *Am. J. Physiol.* 264: C866–C874 (1993)), membrane-associated proteins (Ogawa et al., *Am. J. Physiol.* 262: C546–554 (1992)), enthelin-1 (Gertler et al., *J. Vasc. Surg.* 18: 178–182 (1993)), and platelet aggregating factor (PAF; Caplan et al., *Biochim. Biophy. Acta* 1128: 205–210 (1992)). The origin of the endothelial cells can affect the manner in which they respond to hypoxia (Tretyahkov et al., *Am. J. Physiol.* 265: C770–780 (1993)). In this regard, hypoxia-induced phosphotyrosine has been shown to be markedly blocked by the protein tyrosine kinase inhibitors herbimycin-A and methyl 2,5-dihydroxycinnamate (Koroma et al. (1995), supra) but not by the protein tyrosine kinase inhibitor genistein (Koroma et al. (1995), supra).

Retinal ischemia is currently treated by retinal destruction, primarily by laser photocoagulation. The disadvantages of such treatment are obvious, with loss of visual function dependent on the extent of the retinal destruction required.

Ocular inflammation can occur as a result of disease, bacterial or viral infection, ocular surgery, which includes cataract surgery, retinal surgery, refractive surgery, and corneal surgery, e.g., corneal transplantation, and the like. Ocular inflammation can also occur as a result of corneal transplant rejection.

Cystoid macular edema is a common ocular abnormality resulting from a vast etiology and characterized by perturbation of the integrity of the blood-retinal barrier of the perifoveal capillaries and the optic nerve head. Such perturbation is readily observable as leakage of fluoresceine dye by angiography with accumulation of fluid as microcysts in the outer plexiform layer. Causative etiology includes post-cataract or laser capsulotomy (Irvine-Gass syndrome), uveitis, branch or central vein occlusion, topical epinephrine use, severe hypertension, radiation retinopathy, perifoveal telangectasia and retinitis pigmentosa.

Ocular inflammation is currently treated by corticosteroids. The disadvantages of such treatment are cataracts, increased intraocular pressure, corneal melting, systemic complications, high blood pressure, aseptic necrosis of the femoral head, cardiovascular diseases, facial hair and many others. Nonsteroidal anti-inflammatory compounds are also administered. The disadvantages of such compounds include certain blood diseases, peptic ulcers, gastric distress, and platelet dysfunction with bleeding, and others.

Therefore, there remains a need for methods for the effective prophylactic and therapeutic treatment of retinal ischemia and ocular inflammation. Accordingly, it is a principal object of the present invention to provide a method of prophylactically and therapeutically treating retinal ischemia, such as that associated with occlusion of the central vein, the central artery, a branch vein or a branch artery, or macular edema following ocular surgery, such as cataract surgery, retinal surgery, refractive surgery, and corneal surgery, e.g., corneal transplantation, and the like. It is another principal object of the present invention to provide a method of prophylactically and therapeutically treating ocular inflammation. e.g., macular edema, such as that associated with disease, bacterial or viral infection, or ocular surgery, such as cataract surgery, retinal surgery, refractive surgery, and corneal surgery. e.g., corneal transplantation, and the like, and corneal transplant rejection, among others. These and other objects of the present invention will become apparent from the detailed description provided herein.

BRIEF SUMMARY OF THE INVENTION

The present invention is directed to a method for the prophylactic and therapeutic treatment of retinal ischemia. The present invention is also directed to a method for the prophylactic and therapeutic treatment of ocular inflammation. The methods involve the administration of an inhibitor of the protein tyrosine kinase pathway. Preferably, the inhibitor of the protein tyrosine kinase pathway is a compound of formula:

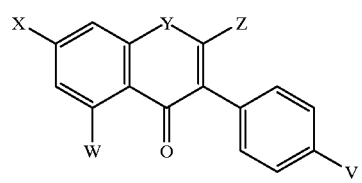

wherein V, W and X are selected from the group consisting of hydro, hydroxyl, alkoxy halo, an ester, an ether, a carboxylic acid group, a pharmaceutically acceptable salt of a carboxylic acid group, and —SR, in which R is hydrogen or an alkyl group, Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

DETAILED DESCRIPTION OF THE INVENTION

The present invention is predicated on the discovery that an inhibitor of the protein tyrosine kinase pathway, specifically genistein, is effective in ameliorating retinal degeneration after ischemia reperfusion injury. Accordingly, the present invention provides a method for the prophylactic and therapeutic treatment of retinal ischemia. In addition, the present invention provides a method for the prophylactic and therapeutic treatment of ocular inflammation. By "prophylactic" is meant the protection, in whole or in part, against retinal ischemia or ocular inflammation. By "therapeutic" is meant the amelioration of retinal ischemia or ocular inflammation, itself, and the protection, in whole or in part, against further retinal ischemia or ocular inflammation, respectively. The present inventive method for the prophylactic and therapeutic treatment of retinal ischemia is particularly useful in the treatment of retinal ischemia due to occlusion of the central vein, the central artery, a branch vein or a branch artery, or macular edema following ocular surgery, such as cataract surgery, retinal surgery, refractive surgery, and corneal surgery, e.g., corneal transplantation, and the like. The present inventive method for the prophylactic and therapeutic treatment of ocular inflammation is particularly useful in the treatment of ocular inflammation, e.g., macular edema, due to disease, bacterial or viral infection, or ocular surgery, such as cataract surgery, retinal surgery, refractive surgery, and corneal surgery. e.g., corneal transplantation, and the like, and corneal transplant rejection, among others. In this regard, the present inventive method is also useful in the treatment of retinal edema associated with, for example, postcataract or laser capsulotomy (Irvine-Gass syndrome), uveitis, branch or central vein occlusion, topical epinephrine use, severe hypertension, radiation retinopathy, perifoveal telangectasia and retinitis pigmentosa.

The methods comprise the administration of an inhibitor of the protein tyrosine kinase pathway in an amount sufficient to treat retinal ischemia or ocular inflammation prophylactically or therapeutically. Any inhibitor of the protein tyrosine kinase pathway can be used in the methods of the present invention as long as it is safe and efficacious. Herein, "PTK inhibitor" will be used to refer to such compounds and is intended to encompass all compounds that affect the protein tyrosine kinase pathway at any and all points in the pathway.

Preferably, the PTK inhibitor is genistein (5,7-dihydroxy-3-(4-hydroxyphenyl)-4H-1-benzopyran-4-one) or a pharmaceutically acceptable, protein tyrosine kinase pathway-inhibiting analogue or prodrug thereof or a pharmaceutically acceptable salt of any of the foregoing. Accordingly, the PTK inhibitor can be a compound of the following formula:

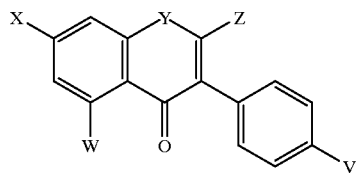

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

The prodrug can be any pharmaceutically acceptable prodrug of genistein, a protein tyrosine kinase pathway-inhibiting analogue of genistein, or a pharmaceutically acceptable salt of either of the foregoing. One of ordinary skill in the art will appreciate, however, that the prodrug used must be one that can be converted to an active PTK inhibitor in or around the retina. A preferred prodrug is a prodrug that increases the lipid solubility of genistein, a protein tyrosine kinase pathway-inhibiting analogue of genistein, or a pharmaceutically acceptable salt of either of the foregoing. A preferred prodrug is one in which one or more of V, W and X are independently derivatized with an ester, such as pivalic acid.

Compounds of the above formula are widely available commercially. For example, genistein is available from LC Laboratories (Woburn. Mass.). Those compounds that are not commercially available can be readily prepared using organic synthesis methods known in the art.

Whether or not a particular analogue, prodrug or pharmaceutically acceptable salt of a compound in accordance with the present invention can treat retinal ischemia prophylactically or therapeutically can be determined by its effect in the rat model used in Example 1. Alternatively, analogues, prodrugs and pharmaceutically acceptable salts of inhibitors of the protein tyrosine kinase pathway can be tested by fluorecein angiography or histology for efficacy in the prophylactic and therapeutic treatment of retinal ischemia and by various animal models. e.g., the rat uveitis model. and by clinical examination, such as by quantitation of cellular and humoral mediators of inflammation for efficacy in the prophylactic and therapeutic treatment of ocular inflammation.

In addition, color Doppler imaging, can be used to evaluate the action of a drug in ocular pathology (Valli et al., *Ophthalmologica* 209(13): 115–121 (1995)). Color Doppler imaging is a recent advance in ultrasonography, allowing simultaneous two-dimension imaging of structures and the evaluation of blood flow. Accordingly. retinal ischemia and ocular inflammation can be analyzed using such technology.

The PTK inhibitor can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable (see e.g., U.S. Pat. Nos. 5,384,333 and 5,164,188).

An advantage of genistein is that it is very safe and efficacious. For example, when genistein was orally administered to Zucker diabetic fatty rats, genistein was found to be nontoxic to the retina at dosages ranging from 75 mg/kg/day to 300 mg/kg/day over a period of six months as measured by electroretinography. In addition, oral administration of genistein was found to have no effect on food intake and body weight for male and female rats. Also, no effect of orally administered genistein was found with respect to the weight of the ovaries and the uterus in female rats.

The PTK inhibitor, which is preferably genistein, a protein tyrosine kinase pathway-inhibiting analogue of genistein, a protein tyrosine kinase pathway-inhibiting prodrug of genistein, or a pharmaceutically acceptable salt of any of the foregoing, can be administered in accordance with the present inventive method by any suitable route. Suitable routes of administration include systemic, such as orally or by injection, topical, periocular (e.g., subTenon's), subconjunctival, intraocular, subretinal, suprachoroidal, and retrobulbar. The manner in which the PTK inhibitor is administered is dependent, in part, upon whether the treatment of retinal ischemia or ocular inflammation is prophylactic or therapeutic. The manner in which the PTK inhibitor is administered for therapeutic treatment of retinal ischemia or ocular inflammation is dependent, in part, upon the cause of the retinal ischemia or ocular inflammation, respectively.

For example, given that occlusion of the central vein, the central artery, a branch vein or a branch artery and macular edema following ocular surgery, such as cataract surgery, retinal surgery, refractive surgery, and corneal surgery, e.g., corneal transplantation, and the like, are major causes of retinal ischemia, the PTK inhibitor can be administered therapeutically as soon as vein occlusion is detected or ocular surgery is completed. The PTK inhibitor can be administered prophylactically before vein occlusion is detected or before, during or after ocular surgery. Similarly, since disease, bacterial or viral infection, ocular surgery, such as cataract surgery, retinal surgery, refractive surgery, and corneal surgery, e.g., corneal transplantation, and the like, and corneal transplant rejection, among others, are major causes of ocular inflammation, e.g., macular edema, the PTK inhibitor can be administered therapeutically as soon as disease or infection is detected or ocular surgery is completed. The PTK inhibitor can be administered prophylactically before disease or infection is detected or before, during or after ocular surgery.

For the prophylactic treatment of retinal ischemia or ocular inflammation, the PTK inhibitor is preferably administered intraocularly or subretinally. In this regard, the use of an intraocular device/implant, such as Vitrasert™, that is bioerodible and bioabsorbable, can be used to achieve sustained release of the PTK inhibitor.

The PTK inhibitor is preferably administered as soon as possible after it has been determined that an animal, such as a mammal, specifically a human, is at risk for retinal ischemia or ocular inflammation (prophylactic treatments) or has begun to develop retinal ischemia or ocular inflammation (therapeutic treatments). Treatment will depend, in part, upon the particular PTK inhibitor used, the amount of the PTK inhibitor administered, the route of administration, and the cause and extent, if any, of retinal ischemia or ocular inflammation realized.

One skilled in the art will appreciate that suitable methods of administering a PTK inhibitor, which is useful in the present inventive method, are available. Although more than one route can be used to administer a particular PTK inhibitor, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular PTK inhibitor employed, the age, species, condition or disease state, and body weight of the animal, as well as the amount of retina about to be affected or actually affected by ischemia or the amount and location of ocular inflammation. The size of the dose also will be determined by the route, timing and frequency of administration as well as the existence, nature, and extent of any adverse side effects that might accompany the administration of a particular PTK inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg/day, if administered systemically. Intraocular administration typically will involve the administration of from about 0.1 mg total to about 5 mg total, preferably from about 0.5 mg total to about 1 mg total. A preferred concentration for topical administration is 100 $\mu$M.

Compositions for use in the present inventive method preferably comprise a pharmaceutically acceptable carrier and an amount of a PTK inhibitor sufficient to treat retinal ischemia or retinal inflammation prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the PTK inhibitor can be formulated as polymeric compositions, inclusion complexes, such as cyclodextrin inclusion complexes, liposomes, microspheres, microcapsules, and the like (see, e.g., U.S. Pat. Nos. 4,997, 652 and 5,718,922).

The PTK inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the PTK inhibitor and one which has no detrimental side effects or toxicity under the conditions of use.

The choice of excipient will be determined in part by the particular PTK inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see *Pharmaceutics and Pharmacy Practice*, J. B. Lippincott Co., Philadelphia. Pa., Banker and Chalmers. eds., pages 238–250 (1982), and *ASHP Handbook on Injectable Drugs*, Toissel, 4th ed., pages 622–630 (1986)). It is preferred that such injectable compositions be administered intramuscularly, intravenously, intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g. U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating, agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening, agents stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443.505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit (e.g., $100\mu$–1 mm in diameter), or an implant or a device comprised of a polymeric composition as described above, can be used.

The present inventive method also can involve the co-administration of other pharmaceutically active compounds. By "co-administration" is meant administration before, concurrently with, e.g., in combination with the PTK inhibitor in the same formulation or in separate formulations, or after administration of a PTK inhibitor as described above. For example, corticosteroids, prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, anti-oxidants, e.g., carotenoids (such as a xanthophyll carotenoid like zeaxanthin or lutein), and micronutrients can be co-administered. In addition, other types of inhibitors of the protein tyrosine kinase pathway, which include natural protein tyrosine kinase inhibitors like quercetin, lavendustin A, erbstatin and herbimycin A, and synthetic protein tyrosine kinase inhibitors like tyrphostins (e.g., AG490, AG17, AG213 (RG50864), AG18, AG82, AG494, AG825, AG879, AG1112, AG1296, AG1478, AG126, RG13022, RG14620 and AG555), dihydroxy- and dimethoxybenzylidene malononitrile, analogs of lavendustin A (e.g., AG814 and AG957), quinazolines (e.g., AG1478), 4,5-dianilinophthalimides, and thiazolidinediones, can be co-administered with genistein or an analogue, prodrug or pharmaceutically acceptable salt thereof (see Levitzki et al., Science 267: 1782–1788 (1995); and Cunningham et al., Anti-Cancer Drug Design 7: 365–384(1992)). In this regard, potentially useful derivatives of genistein include those set forth in Mazurek et al., U.S. Pat. No. 5,637,703. Neutralizing proteins to growth factors, such as a monoclonal antibody that is specific for a given growth factor, e.g., VEGF (for an example, see Aiello et al., PNAS USA 92: 10457–10461 (1995)), or phosphotyrosine (Dhar et al., Mol. Pharmacol. 37: 519–525 (1990)), can be co-administered. Other various compounds that can be co-administered include protein kinase C inhibitors (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNFα, an anti-proliferative peptide, e.g., SPARC and prolferin-like peptides, a glutamate receptor antagonist, aminoguanidine, an angiotensin-converting, enzyme inhibitor, e.g., angiotensin II, calcium channel blockers, Ψ-tectorigenin, ST638, somatostatin analogues, e g., SMS 201-995, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638 (Asahi et al., FEBS Letter 309: 10–14 (1992)), thalidomide, nicardipine hydrochloride, aspirin, piceatannol, staurosporine. adriamycin, epiderstatin, (+)-aeroplysinin-1, phenazocine, halomethyl ketones, anti-lipidemic agents, e.g., etofibrate, chlorpromazine and spinghosines, aldose reductase inhibitors, such as tolrestat, SPR-210, sorbinil or oxygen, and retinoic acid and analogues thereof (Burke et al., Drugs of the Future 17(2): 119–131 (1992); and Tomlinson et al., Pharmac. Ther. 54: 151–194 (1992)). Selenoindoles (2-thioindoles) and related disulfide selenides, such as those described in Dobrusin et al., U.S. Pat. No. 5,464,961, are useful protein tyrosine kinase inhibitors.

EXAMPLE

The following example further illustrates the present invention but, of course, should not be construed as in any way limiting its scope.

Example 1

This example demonstrates that genistein ameliorates retinal degeneration after ischemia reperfusion injury.

Eighty adult male Sprague-Dawley rats (200–250 g body weight each) were operated on as described previously (Hayashi et al. (1996), supra). Only one eye of each rat was operated on in accordance with procedures that conformed to The Association for Research in Vision and Ophthalmology (ARVO) Statement for the Use of Animals in Ophthalmic and Vision Research. Briefly, rats were anesthetized with chloral hydrate (400 mg/kg). Then, the conjunctiva of the eye was dissected temporally, the lateral rectus muscle was removed, and the optic nerve was exposed with blunt forceps. A ligature of 4-0 silk was placed on the optic nerve, and the ligature was tightened while the surgeon watched, using an operating microscope, for blood flow in the retinal vessels to stop. When cessation of blood flow was confirmed, the eyelids were sutured with 6-0 silk (to protect the cornea from drying during ischemia). After two hours, the sutures in the eyelids were removed and the retinal vessels were examined, while under the operating microscope, to confirm nonperfusion. Then, the ligature was removed and the retinal vessels were allowed to reperfuse. Only those eyes in which reperfusion was confirmed within ten minutes after removal of the ligature were used in the experiments. A sham operation was not performed because it had been previously shown that it induces no change in protein profiles or tyrosine-phosphorylated proteins (Hayashi et al. (1996), supra).

Genistein (LC laboratories, Woburn, Mass.) was dissolved in dimethyl sulfoxide (DMSO) and injected into the intraperitoneal space of each rat in the amount of 0.034 mg, 0.34 mg or 3.4 mg. The volume of DMSO used for dissolving genistein was adjusted to 0.34 ml for each amount of genistein. As a control, 0.34 ml of DMSO alone was intraperitoneally injected into rats. The three different amounts of genistein or DMSO alone were administered to each rat twice. The first injection was performed one hour before the induction of the ischemia-reperfusion injury and the second injection was performed just after confirmation of the reperfusion of the retinal blood vessels after two hours of ischemia. All rats treated with the three different amounts of genistein or DMSO alone appeared to be normal in general condition and behavior. The rats were killed after 48 hr of reperfusion for Western blot analysis or after 168 hr for morphometric studies.

The eyes were enucleated and the anterior segments and the vitreous were removed. The retinas were dissected away from the choroid and prepared as previously described (Hayashi et al. (1996), supra; Koroma et al. (1994), supra; and Koroma et al. (1995), supra). Briefly, isolated retinas were immersed in ice-cold lysis buffer (150 mM NaCl, 1% Triton X-100, 0.5% sodium deoxycholate, 0.1% sodium dodecyl sulfate (SDS), 50 mM Tris, 100 $\mu$g/ml phenylmethylsulfonyl fluoride. 0.3 $\mu$g/ml EDTA. 0.7 $\mu$g/ml pepstatin A, 0.5 $\mu$g/ml leupeptin, 1 mM orthovanadate, and 50 $\mu$M sodium fluoride) and homogenized. An equal amount of 2× SDS sample butter (160 mM Tris, pH 6.8. 4% SDS, 30% glycerol, 5% β-mercaptoethanol, 10 mM dithiothreitol and 0.01% bromophenol blue) was added to the lysate. The samples were boiled at 95° C. for 5 min. Then, the samples were centrifuged at 13,00 rpm for 1 min and the supernatants were collected. Samples were stored at −80° C. until use for gel electrophoresis. Thirty-two eyes of 32 rats in which ischemia-reperfusion injury was induced (eight eyes of eight rats for treatment with each amount of genistein) and eight eyes of eight rats, which were not operated upon (normal control), were used to prepare retinal samples for gel electrophoresis. Protein concentrations were measured by the Pierce BCA method. Equal amounts of protein in each of the samples were electrophoresed by SDS-polyacrylamide gel electrophoresis.

The samples were run on 4% to 20% gradient minigels (Bio-Rad Laboratories, Hercules, Calif.) on a Bio-Rad Protean II apparatus. Biotinylated and prestained molecular markers (Bio-Rad) were run with the samples simultaneously. After electrophoresis, gels were processed either for total protein staining with Coomassie brilliant blue dye or for Western blot analysis.

After electrophoresis, the gels were fixed in 45% methanol and 10% acetic acid aqueous solution for 30 min. They were soaked in saturated picric acid solution briefly and stained with 0.25% aqueous Coomassie brilliant blue (R-250) for a minimum of two hours. The gels were destained in 10% acetic acid solution. Coomassie blue staining of gels after electrophoresis was performed using eight separate sets of retinal samples. One set of retinal samples included one normal retina and four ischemia-reperfusion-injured retinas, each of which was treated with DMSO alone or 0.034 mg, 0.34 mg or 3.4 mg of genistein.

Coomassie blue staining of gels after electrohoresis was repeated three time with one set of retinal samples from the eyes after 48 hrs of reperfusion after 2 hrs of ischemia. A total of eight separate sets of retinal samples were examined.

Treatment with genistein caused a change in total protein profiles. A 72 kDa band was increased in ischemia reperfusion-injured retinas treated with DMSO alone as compared to the normal retina. However, this band did not increase detectably after the injury if the rats were treated with 0.034 mg, 0.34 mg or 3.4 mg genistein. Other bands in the total protein profiles looked similar, irrespective of the treatment. The observed change of the 72 kDa band was obtained and confirmed eight times with eight separate sets of retinal samples.

Those gels that were to be analyzed by Western blot were electroblotted onto nitrocellulose membrane (Costar Scientific Cambridge. Mass.) with the use of a transblot SD apparatus (Bio-Rad). The membranes for detection of tyrosine-phosphorylated proteins were incubated with 3% bovine serum albumin in Tris-buffered saline (20 mM Tris and 150 mM NaCl, pH 7.5) for 1 hr at room temperature. Then, each membrane was incubated with a primary antibody solution (mouse monoclonal antiphosphotyrosine antibody (PY69) (1:500 dilution) obtained from Transduction Laboratories (Lexington, Ky.)) at 4° C. overnight. The membranes were rinsed three times with Tris-buffered saline and then incubated with a solution of horseradish peroxidase-conjugated rat anti-mouse immunoglobulin G antibody (Jackson Immunoresearch Laboratories, West Grove, Pa.) (1:1,000 dilution) and avidin-horseradish peroxidase (Bio-Rad) (1:15,000 dilution) for 2 hr at room temperature. After the membranes had been rinsed three times with Tris-buffered saline containing 0.3% Tween 20 and twice with Tris-buffered saline they were incubated with enhanced chemiluminescence reagents (Amersham Life Science, Arlington Heights, Ill.) and exposed to Kodak x-ray films (Eastman Kodak, Rochester, N.Y.) for 15 seconds to 5 minutes, as described in Amersham-enhanced chemiluminescence protocols.

Western blot analysis of tyrosine-phosphorylated proteins was repeated at least three times with one set of retinal samples. Fight separate sets of retinal samples were examined for Western blot analysis for tyrosine-phosphorylated proteins.

The eight separate sets of retinal samples that were studied by Western blot analysis with antiphosphotyrosine antibody PY69 revealed an increase in tyrosine-phosphorylated proteins in ischemia reperfusion-injured retinas treated with DMSO alone in comparison to normal retinas. Two bands (66 and 15 kDa) were increased in the injured eyes treated with DMSO alone or 0.034 mg, genistein. Only the 66 kDa band showed a gradual decrease as the dose of genistein increased. The 15 kDa band appeared to increase with a low dose of genistein and decreased with high doses of genistein. The 110 kDa band was not chanced significantly by treatment with genistein. Treatment with 3.4 mg genistein inhibited overall increase in tyrosine-phosphorylated proteins in the retina induced by ischemia-reperfusion injury. The apparent changes of the 66 kDa and 15 kDa bands in Western blots of tyrosine-phosphorylated proteins were confirmed eight times with the eight separate sets of retinal samples.

After the eyes were enucleated and a small incision made at the corneoscleral limbus, the eyes were fixed in 2% paraformaldehyde and 2% glutaraldehyde in 0.1 M phosphate buffer overnight at 4° C. The anterior portions were removed and the eyes were divided into half along the horizontal meridian, including the optic disc, and post-fixed in 1% osmium tetroxide. The tissues were rinsed in 0.1 M phosphate buffer, and then the tissues were dehydrated through a graded series of ethanol. The tissues were placed in two changes of propylene oxide for 15 min each and infiltrated overnight in a 1:1 solution of propylene oxide and LX112 resin (Ladd Research Industries, Burlington, Vt.). The tissues were then embedded in 100% LX112 resin. For light microscopic morphometry, the eyes were cut in 1 $\mu$m sections and then stained with 0.4% toluidine blue and 0.25% sodium borate. Each section was cut along the horizontal meridian through the optic nerve head. Sections were cut perpendicularly to the retinal surface. Oblique sections, which appeared to have an artifactually thicker retina and shortened rod outer segments, were excluded.

Retinas were morphometrically analyzed as described previously (Weber et al., Invest. *Ophthtalmol. Vis. Sci.* 37: 267–273 (1996): and Hughes, *Exp. Eye Res.* 53: 573–582 (1991)). Six eyes of six rats were used for each treatment (total of 24 rats for four groups). Six normal rats that were not operated on were used for presenting normal values of the retina. Using a scale on the eyepiece lens, the thickness of retinal layers in each section was measured in the retina at a distance of 1.5 mm from the center of the optic nerve head as described previously. The thickness of four different retinal layers was measured to evaluate ischemic retinal damage: the thickness from the inner limiting membrane to the outer limiting membrane (ILM-OLM), the inner plexiform layer (IPL), the inner nuclear layer (INL), and the outer nuclear layer (ONL). The values of retinal thickness were averaged from ten measurements of five sections in each eye, and one average value per each layer was obtained from each eye.

After 168 hr of reperfusion, the retinas of rats treated with DMSO alone showed a severe degeneration, especially in the inner retina as compared with that of the normal retina. The retinas of rats treated with 0.034 mg genistein showed a similar degree of degeneration as those treated with DMSO alone. The ONL of the eyes treated with DMSO alone or 0.034 mg genistein had a similar degree of edema and number of pyknotic nuclei. Treatment with 0.34 mg genistein resulted in a slightly more preserved retina, especially in the INL, when compared with that of the rats treated with DMSO alone. The rats treated with 3.4 mg genistein had a well-reserved retinal structure, which appeared nearly normal, especially in the IPL and the INL. The ganglion cells in the retina of rats treated with 3.4 mg genistein were protected moderately from neuronal degeneration when compared with those of the rats treated with DMSO alone, but the ganglion cells showed moderate degenerative changes when compared with those of the normal retinas.

In order to quantify the degree of retinal cell loss, the number of cell nuclei per 50 μg of length in retinal sections as linear cell densities was counted. The number of cell nuclei of three retinal layers (ganglion cell layer (GCL), INL and ONL) was counted in the width of 50 μm in the retina from both hemispheric sections at a distance of 1.5 mm from the optic nerve head. The average value was taken in the same manner as described above.

The measurement of retinal thickness and retinal cell densities was performed by two individuals under masked conditions. Data are expressed as the mean±standard deviation. Statistical differences among multiple treatment groups were assessed with nonparametric one-way analysis of variance (Kruskal-Wallis test/Dunn's method), and P<0.05 was considered to be statistically significant.

After 168 hrs of reperfusion, three parameters of retinal thickness, i.e., ILM-OLM, IPL and INL, showed a dose-dependent rescue effect, i.e., retinal thickening toward normal values, of treatment with genistein. The retinas treated with 3.4 mg genistein had significantly higher values than those treated with DMSO alone or 0.034 mg genistein. The average thickness of ILM-OLM of the rats treated with 3.4 mg genistein was 137.8±8.3 μm and was significantly thicker (P<0.02) than that of the rats treated with DMSO alone (80.5±17.5 μm) or 0.034 mg of genistein (90.1±21.0 μm). The average thickness of ILM-OLM of the rats treated with 3.4 mg genistein showed 90% of that of normal, nontreated rat retinas, whereas the thickness of ILM-OLM of the rats treated with DMSO alone or 0.034 mg genistein was 52.6% and 58.9% of that of normal, nontreated rat retinas, respectively. The average thickness of IPL of the rats treated with 3.4 mg genistein (36.8±8.6 μm) was significantly thicker (P<0.02) than that of the rats treated with DMSO alone (15.3±8.3 μm) or 0.034 mg genistein (12.9±4.3 μm). The average thickness of IPL, of the rats treated with 3.4 mg genistein showed 66.9% of that of normal, nontreated rat retinas, whereas the thickness of IPL of the rats treated with DMSO alone or 0.034 mg genistein was 29.1% and 24.7% of that of normal, nontreated rat retinas, respectively. The average thickness of INL of the rats treated with 3.4 mg genistein (31.1±2.3 μm) was significantly thicker (P<0.02) than that of the retinas of rats treated with 0.034 mg genistein (15.8±6 μm). The thickness of INL of the rats treated with 3.4 mg of genistein showed 110.2% of that of normal, nontreated rat retinas, whereas the thickness of INL of the rats treated with 0.034 mg genistein was 55.8% of that of normal, nontreated rat retinas. The ONL thickness increased slightly in the eyes after the injury, but no significant change was detected in any treatment group.

Cell density analysis of the retinas after ischemia-reperfusion injury revealed that the rats treated with DMSO alone or 0.034 mg genistein showed a severe loss of retinal cells, especially in GCL and INL. Treatment with genistein partially protected GCL and INL in a dose-dependent manner, and the changes in linear cell densities appeared to correspond to the changes in thickness of the retinal layers; however, the statistical analysis showed that treatment with any dose of genistein did not cause statistically significant protection in the cell densities of GCL and INL. The cell densities of ONL in the rats treated with DMSO alone or genistein were not changed significantly after the injury.

The above results show that treatment with genistein inhibited increases in tyrosine phosphorylation after ischemia-reperfusion injury. In addition, treatment with genistein protected against subsequent neuronal degeneration.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of prophylactically or therapeutically treating an animal for retinal ischemia, which method comprises administering to said animal an inhibitor of the protein tyrosine kinase pathway in an amount sufficient to treat said animal for retinal ischemia prophylactically or therapeutically.

2. The method of claim 1, wherein said inhibitor of the protein tyrosine kinase pathway is a compound of formula:

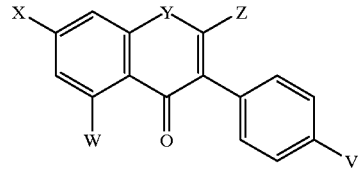

wherein V, W and X are selected from the group consisting of hydro, alkoxy, hydroxyl, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl, or a protein tyrosine kinase-inhibiting prodrug or pharmaceutically acceptable salt thereof.

3. The method of claim 2, wherein the halo group is selected from the group consisting of fluorine, chlorine and bromine.

4. The method of claim 2, wherein the ester is a C$_1$–C$_6$ ester.

5. The method of claim 2, wherein the ether is a C$_1$–C$_6$ ether.

6. The method of claim 2, wherein said pharmaceutically acceptable salt of a carboxylic acid group is a sodium salt or a potassium salt.

7. The method of claim 2, wherein the alkyl groups are C$_1$–C$_6$ alkyl groups and the alkoxy group is a C$_1$–C$_6$ alkoxy group.

8. The method of claim 2, wherein said inhibitor of the protein tyrosine kinase pathway is genistein.

9. The method of claim 1, wherein said retinal ischemia is that which results from occlusion of the central vein, the central artery, a branch vein or a branch artery or that which results from macular edema that results from ocular surgery.

10. The method of claim 2, wherein said retinal ischemia is that which results from occlusion of the central vein, the central artery, a branch vein or a branch artery or that which results from macular edema that results from ocular surgery.

11. The method of claim 8, wherein said retinal ischemia is that which results from occlusion of the central vein, the central artery, a branch vein or a branch artery or that which results from macular edema that results from ocular surgery.

12. The method of claim 11, wherein genistein is administered topically, subconjunctivally, retrobulbarly, periocularly, subretinally, suprachoroidally or intraocularly.

13. The method of claim 12, wherein genistein is administered by a mechanical reservoir, device or implant.

14. The method of claim 12, wherein genistein is administered intraocularly in an amount from about 0.1 mg total to about 5 mg total.

15. The method of claim 14, wherein genistein is administered intraocularly in an amount from about 0.5 mg total to about 1 mg total.

16. A method of prophylactically or therapeutically treating an animal for ocular inflammation, which method comprises administering to said animal an inhibitor of the protein tyrosine kinase pathway in an amount sufficient to treat said animal for ocular inflammation prophylactically or therapeutically.

17. The method of claim 16, wherein said inhibitor of the protein tyrosine kinase pathway is a compound of formula:

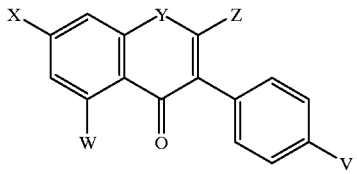

wherein V, W and X are selected from the group consisting of hydro, alkoxy, hydroxyl, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl, or a protein tyrosine kinase-inhibiting prodrug or pharmaceutically acceptable salt thereof.

18. The method of claim 17, wherein the halo group is selected from the group consisting of fluorine, chlorine and bromine.

19. The method of claim 17, wherein the ester is a $C_1$–$C_6$ ester.

20. The method of claim 17, wherein the ether is a $C_1$–$C_6$ ether.

21. The method of claim 17, wherein said pharmaceutically acceptable salt of a carboxylic acid group is a sodium salt or a potassium salt.

22. The method of claim 17, wherein the alkyl groups are $C_1$–$C_6$ alkyl groups and the alkoxy group is a $C_1$–$C_6$ alkoxy group.

23. The method of claim 17, wherein said inhibitor of the protein tyrosine kinase pathway is genistein.

24. The method of claim 16, wherein said ocular inflammation is that which results from a disease.

25. The method of claim 16, wherein said ocular inflammation is that which results from a bacterial or viral infection.

26. The method of claim 16, wherein said ocular inflammation is that which results from ocular surgery.

27. The method of claim 26, wherein said ocular surgery is cataract surgery, retinal surgery, refractive surgery, or corneal surgery.

28. The method of claim 27, wherein said corneal surgery is corneal transplantation.

29. The method of claim 28, wherein said corneal transplantation results in corneal transplant rejection.

30. The method of claim 16, wherein said ocular inflammation is nondiabetic macular edema.

31. The method of claim 17, wherein said ocular inflammation is that which results from a disease.

32. The method of claim 17, wherein said ocular inflammation is that results from a bacterial or viral infection.

33. The method of claim 17, wherein said ocular inflammation is that which results from ocular surgery.

34. The method of claim 33, wherein said ocular surgery is cataract surgery, retinal surgery, refractive surgery, or corneal surgery.

35. The method of claim 34, wherein said corneal surgery is corneal transplantation.

36. The method of claim 35, wherein said corneal transplantation results in corneal transplantation rejection.

37. The method of claim 17, wherein said ocular inflammation is nondiabetic macular edema.

38. The method of claim 23, wherein said ocular inflammation is that results from a disease.

39. The method of claim 23, wherein said ocular inflammation is that which results from a bacterial or viral infection.

40. The method of claim 23, wherein said ocular inflammation is that which results from ocular surgery.

41. The method of claim 40, wherein genistein is administered topically, subconjunctivally, retrobulbarly, periocularly, subretinally, suprachoroidally or intraocularly.

42. The method of claim 41, wherein genistein is administered intraocularly in an amount from about 0.1 mg total to about 5 mg total.

43. The method of claim 42, wherein genistein is administered intraocularly in an amount from about 0.5 mg total to about 1 mg total.

44. The method of claim 40, wherein said ocular surgery is cataract surgery, retinal surgery, refractive surgery, or corneal surgery.

45. The method of claim 44, wherein genistein is administered topically, subconjunctivally, retrobulbarly, periocularly, subretinally, suprachoroidally or intraocularly.

46. The method of claim 45, wherein genistein is administered intraocularly in an amount from about 0.1 mg total to about 5 mg total.

47. The method of claim 46, wherein genistein is administered intraocularly in an amount from about 0.5 mg total to about 1 mg total.

48. The method of claim 44, wherein said corneal surgery is corneal transplantation.

49. The method of claim 48, wherein genistein is administered topically, subconjunctivally, retrobulbarly, periocularly subretinally, suprachoroidally or intraocularly.

50. The method of claim 49, wherein genistein is administered intraocularly in an amount from about 0.1 mg total to about 5 mg total.

51. The method of claim 50, wherein genistein is administered intraocularly in an amount from about 0.5 mg total to about 1 mg total.

52. The method of claim 48, wherein said corneal transplantation results in corneal transplant rejection.

53. The method of claim 23, wherein said ocular inflammation is nondiabetic macular edema.

54. The method of claim 53, wherein genistein is administered topically, subconjunctivally, retrobulbarly, periocularly, subretinally, suprachoroidally or intraocularly.

55. The method of claim 54, wherein genistein is administered intraocularly in an amount from about 0.1 mg total to about 5 mg total.

56. The method of claim 55, wherein genistein is administered intraocularly in an amount from about 0.5 mg total to about 1 mg total.

* * * * *